(12) United States Patent
Young et al.

(10) Patent No.: US 11,648,195 B2
(45) Date of Patent: May 16, 2023

(54) COSMETIC COMPOSITION FOR IMPROVING SKIN CONDITION CONTAINING PEONY EXTRACT AS ACTIVE INGREDIENT FOR HEATSHOCK PROTEIN ACTIVATION

(71) Applicant: BioStandard Inc., Seoul (KR)

(72) Inventors: Yoon Ji Young, Seoul (KR); Kim Woo Jin, Seoul (KR)

( * ) Notice: Subject to any disclaimer, the term of this patent is extended or adjusted under 35 U.S.C. 154(b) by 0 days.

(21) Appl. No.: 17/236,377

(22) Filed: Apr. 21, 2021

(65) Prior Publication Data

US 2021/0322294 A1    Oct. 21, 2021

(30) Foreign Application Priority Data

Apr. 21, 2020   (KR) ..................... 10-2020-0048373

(51) Int. Cl.
*A61K 8/81*      (2006.01)
*A61K 8/9783*    (2017.01)

(52) U.S. Cl.
CPC .......... *A61K 8/8105* (2013.01); *A61K 8/9783* (2017.08)

(58) Field of Classification Search
CPC .................................................. A61K 8/8105
See application file for complete search history.

(56) References Cited

U.S. PATENT DOCUMENTS

| 8,101,209 B2 * | 1/2012 | Legrand | A61P 9/08 |
| 2010/0204093 A1 * | 8/2010 | Kaushal | A61K 41/00 |
| | | | 514/19.5 |

* cited by examiner

*Primary Examiner* — Benjamin J Packard
(74) *Attorney, Agent, or Firm* — Rumit Ranjit Kanakia

(57) ABSTRACT

The present invention relates to a cosmetic composition which includes microcapsule particles (1 to 1,000 μm) stabilized by encapsulating a peony extract as an active ingredient, which is useful for skin, with a biocopolymer, and a fibrous protein surrounding the particles in a matrix form, a method of preparing the cosmetic composition, and the use of the cosmetic composition for improving a skin condition.

8 Claims, 8 Drawing Sheets

MIX BIOCOPOLYMER WITH BASIC AMINO ACID
▓ BIOCOPOLYMER    ◈ BASIC AMINO ACID

ADD ACTIVE INGREDIENT AND STIR
△ ACTIVE INGREDIENT

ADD POLYGLYCERYL ESTER AND STIR
○ POLYGLYCERYL ESTER

ADD FIBROUS PROTEIN AND STIR
✧ MICROCAPSULE
∼ FIBROUS PROTEIN MATRIX

[Figure 1]
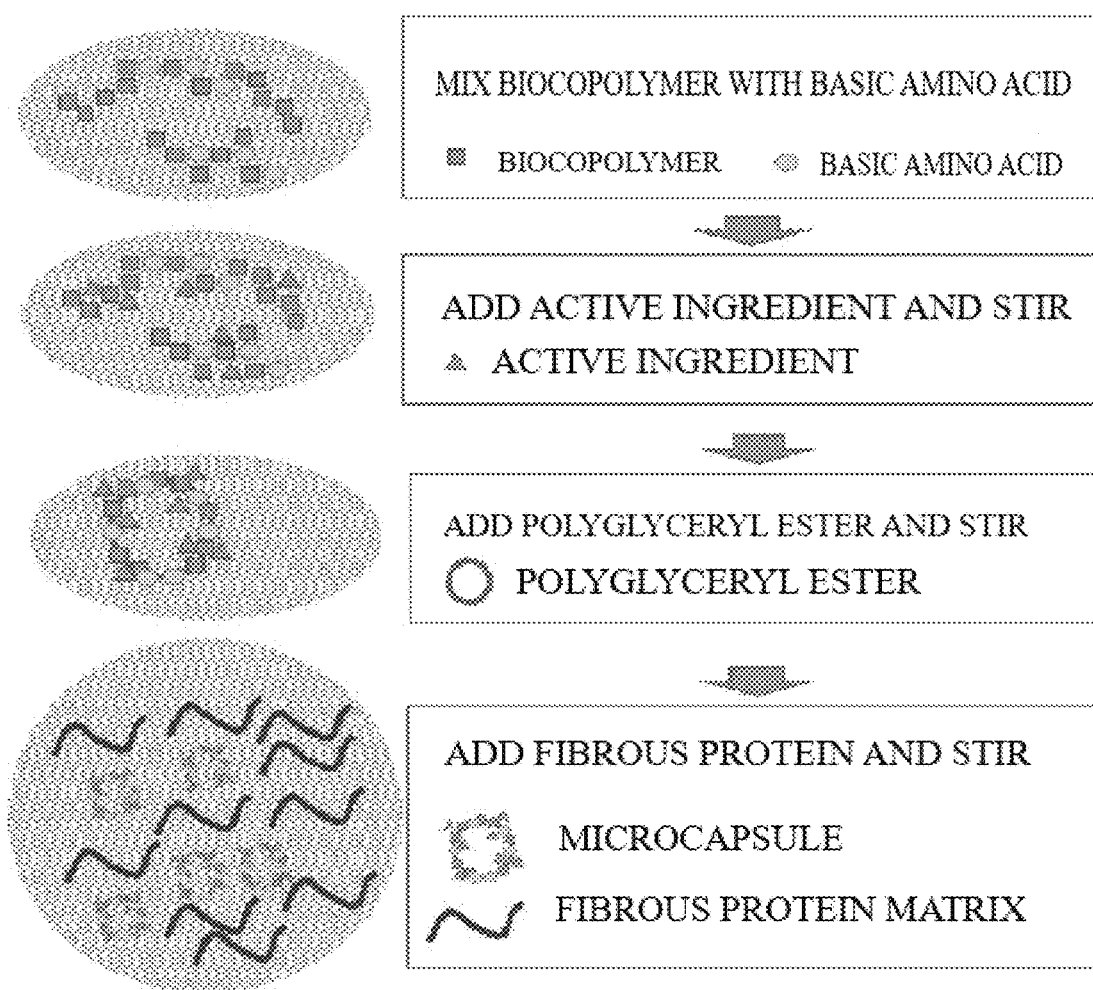

[Figure 2]
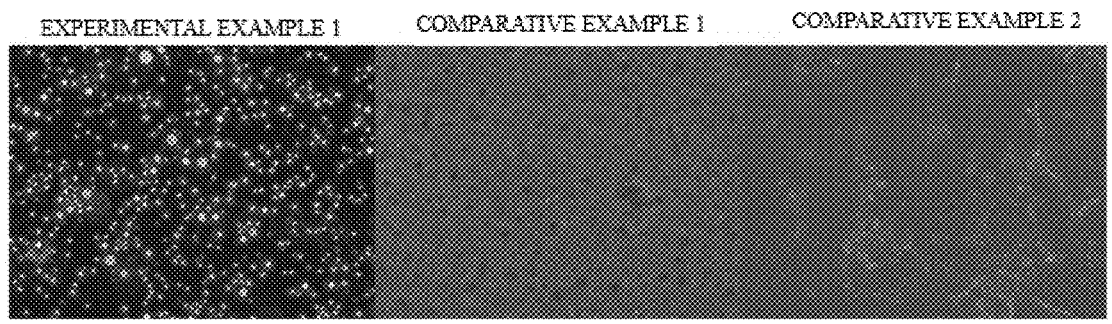

[Figure 3]
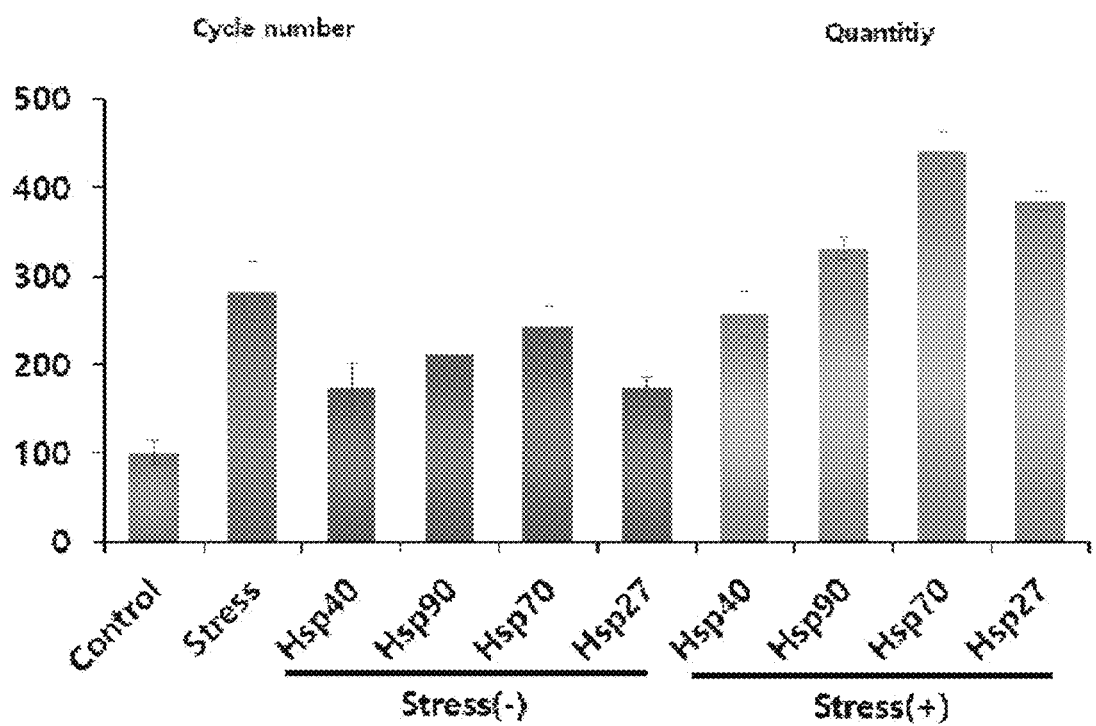

[Figure 4]
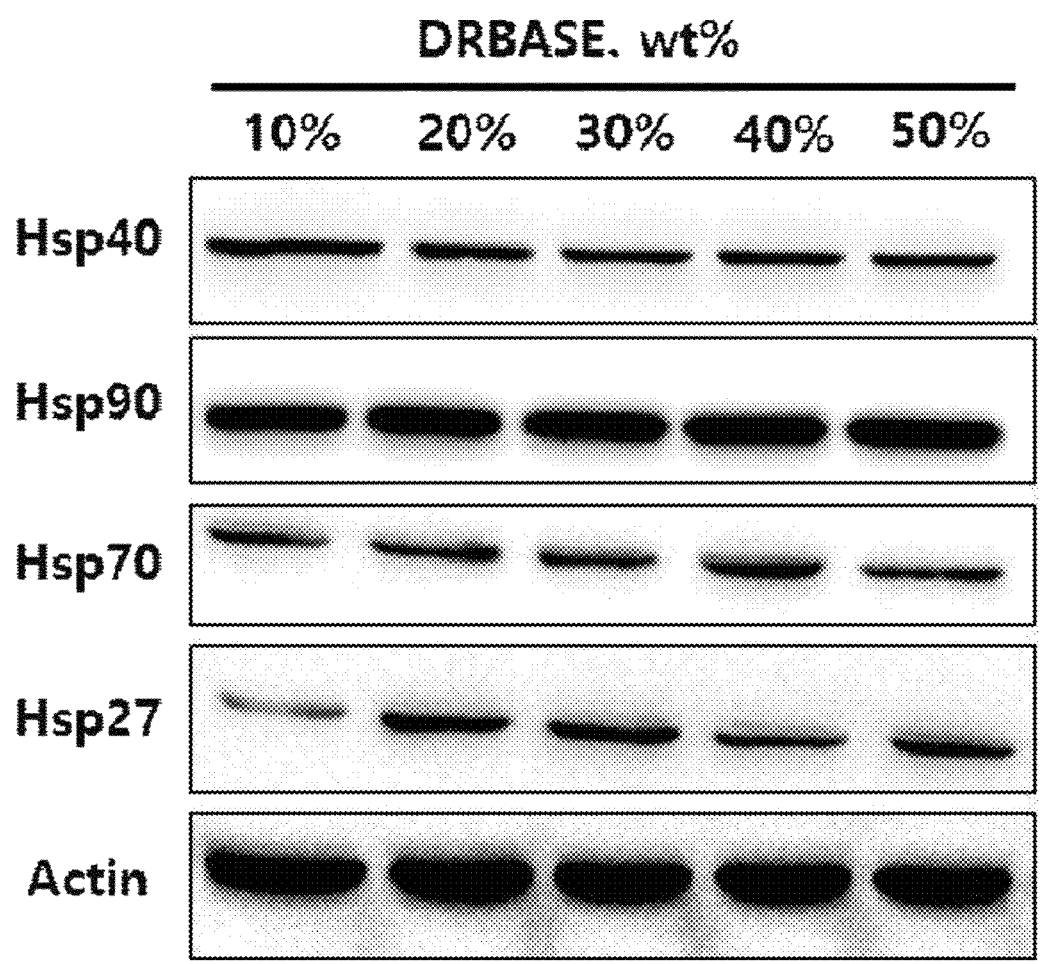

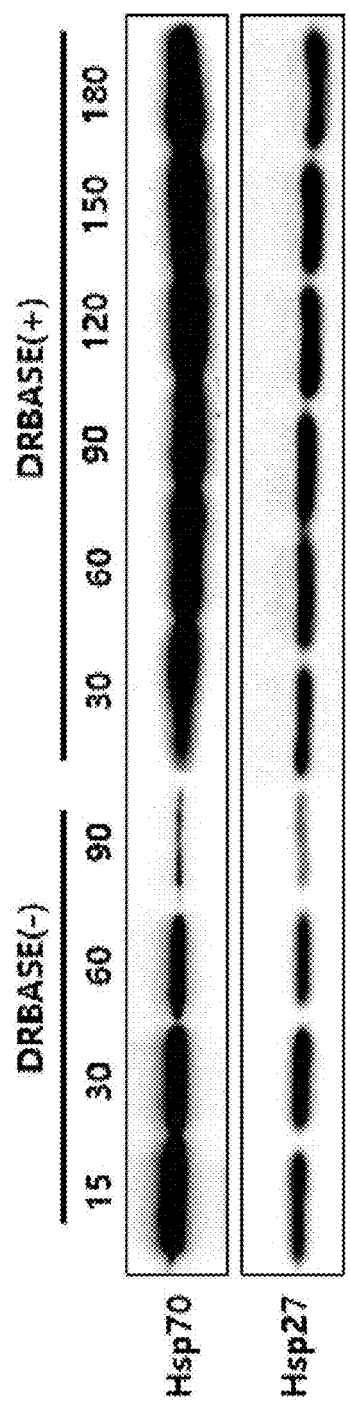
[Figure 5]

[Figure 6]
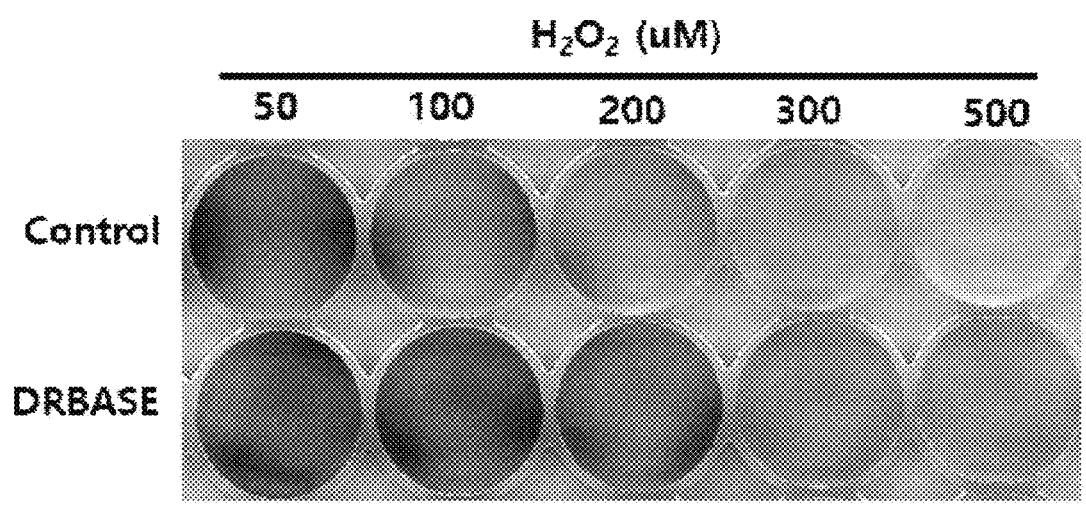

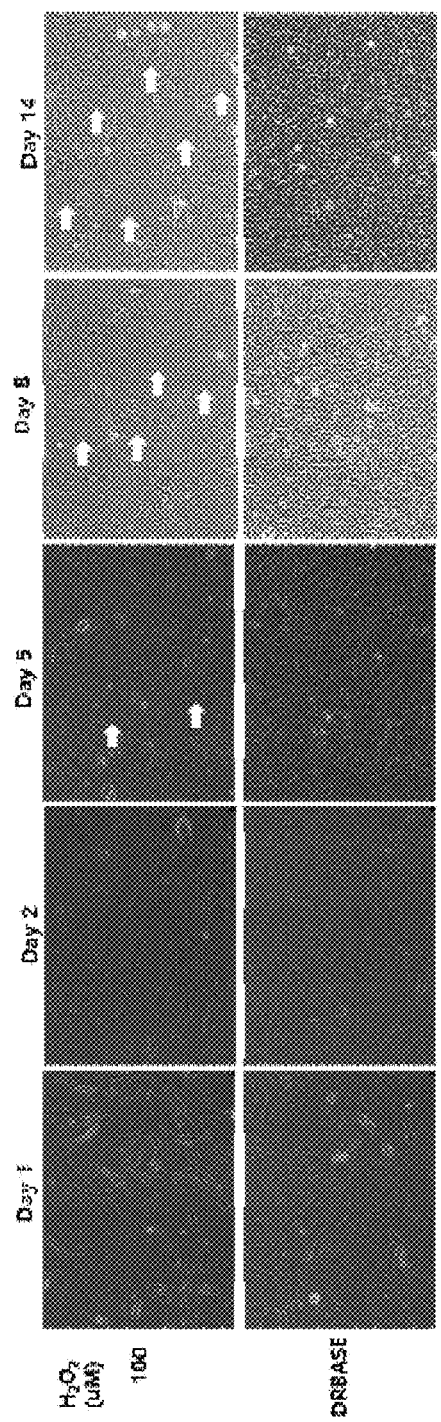
[Figure 7]

[Figure 8]
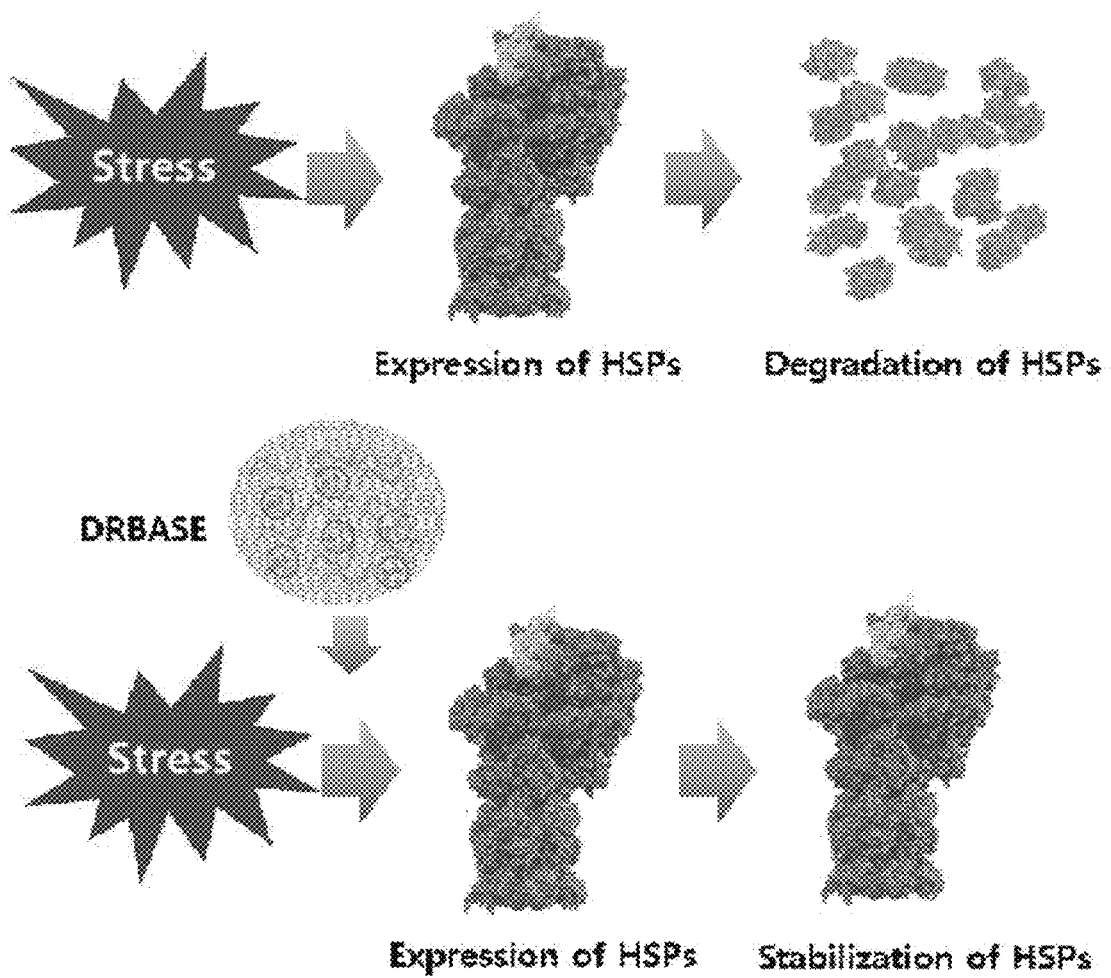

COSMETIC COMPOSITION FOR IMPROVING SKIN CONDITION CONTAINING PEONY EXTRACT AS ACTIVE INGREDIENT FOR HEATSHOCK PROTEIN ACTIVATION

CROSS-REFERENCE TO RELATED APPLICATION

This application claims priority to and the benefit of Korean Patent Application No. 10-2020-0048373, filed on 2020 Apr. 21. the disclosure of which is incorporated herein by reference in its entirety.

BACKGROUND

1. Field of the Invention

The present invention relates to a cosmetic composition which includes microcapsule particles (1 to 1000 μm) which are stabilized by encapsulating a peony extract as an active ingredient, which is useful for skin, with a biocopolymer, and a fibrous protein surrounding the particles in a matrix form, a method of preparing the cosmetic composition and the use of the cosmetic composition for improving a skin condition.

2. Discussion of Related Art

Human skin undergoes continuous changes, and among these, the major changes are the decline in skin function and visual beauty due to aging. Skin aging is largely divided into internal aging caused by genetic factors and external aging caused by external environmental factors such as sunlight. The external aging makes wrinkles in skin, and representative wrinkle-forming factors include reactive oxygen species, UV and the reduction in biosynthesis of collagen.

It is impossible to artificially regulate the internal skin aging, but, in the case of external aging, aging may be prevented, treated or delayed by removing free radicals, proliferating fibroblasts and promoting collagen biosynthesis.

A heat shock protein (hereinafter, HSP) is a protein that is synthesized when cells, tissue or an individual is exposed to a temperature higher than a physiological temperature. Such proteins are named according to their molecular weight in units of kilodaltons, such as HSP60, HSP70, HSP90 and the like, and vary in characteristics according to molecular weight. HSP, as a chaperone, binds to a protein that does not form a complete steric structure so that it serves to prevent intermolecular aggregation and promote regeneration. Therefore, cells that accumulates HSPs in large quantities show resistance to high temperature. The chaperone function of these HSPs is used in normal cells, and HPSs also bind to an immature protein immediately after synthesis to play important roles in the formation of a higher-order structure, intracellular transport, and the membrane permeation of cell organelles. Therefore, representative HSPs are also essential for cells to live under normal conditions, not high temperature or other stressful conditions. Another important function of HSPs is to decompose a denatured protein. Ubiquitin is also a representative HSP, but when covalently bound to a denatured protein, serves as a marker for decomposition by a proteasome.

HSPs may serve to prevent oxidation. It serves as a redox sensor, senses and activates oxidative stress, serves to prevent damage to major intracellular proteins, and suppresses necrosis caused by denaturation of proteins caused by reactive oxygen species or oxidation of a membrane lipid.

HSPs may prevent aging. In keratinocytes constituting the stratum corneum of the skin, HSPs protect cells from stress such as UV, restore cell functions, exhibit an excellent aging-inhibitory function of dermal cells, improve regenerative ability and dermal immunity, help in preventing pigmentation and maintaining healthy skin and skin tissue, and induce regeneration of scars and damaged skin. A HSP is a growth factor essential for healthy and refreshing aged skin.

*Paeonia lactiflora* grows on mountains. It has several stems coming out of one plant and stands upright, is approximately 60 cm high, and has no hair on leaves and stems. It has several roots, which are however formed in a thick pointed cylinder-shape with thin and elongated ends. The leaves are alternate, and each in the lower part is a compound leaf consisting of three leaflets coming out twice. A leaflet is formed in a lanceolate or oval shape, sometimes splits into two to three pieces, and has red veins and petioles. A leaf in the upper part has a simple shape, and a single leaf consisting of three leaflets. The leaf has a glossy surface, a light green backside, and a blunt edge. One flower blooms at the end of a stem in May or June, and is large and beautiful, and a cultivated one has a diameter of approximately 10 cm. The colors of flowers vary, for example, red, white, etc., and there are many horticultural varieties. There are five green calyxes which have flat edges and remain until the end, but the outermost one is in a leaf shape. *Paeonia lactiflora* has approximately 10 petals, but basic species have 8 to 13 petals, which are formed in the shape of an upside down egg and have a length of approximately 5 cm. It has numerous yellow stamens, and 3 to 5 pistils each of which has a stigma tilted back, and an egg-shaped ovary has little or no hair. Fruits are egg-shaped, hooked at the end and split along the inner seam, and seeds are spherical. Flowers are very beautiful and used for horticulture. Roots are used as a medicine for pain, abdominal pain, menstrual pain, amenorrhea, hematopoiesis, anemia and bruises. *Paeonia lactiflora* was cultivated as an ornamental plant in the Qin and Ming dynasties of China, and was cultivated longer than *Paeonia suffruticosa*. From Song to Qing dynasties in China, dozens of species were recorded. It is distributed in Korea, Mongolia and East Siberia.

A peony extract is a monoterpene glycoside with a pinane structure, having paeoniflorin as a main ingredient. Peonies are commercialized as herbal medicine after drying and processing, and a conventional drying method used in Korean peony farms is natural drying after pulverization, but due to a long drying time, thermal drying (briquette drying or hot air drying) is widely used. In China and Japan, a steaming and drying method is also used. Natural drying is used to maintain the original color and smell, and is advantageous for maintaining active ingredients.

Paeoniflorin is extracted with water or a liquid mixture of water and an alcohol in a high yield of 90% or more, but is not well extracted in a pure alcohol.

Paeoniflorin is known as a relatively stable compound, and thus there is no report on the destruction or loss of paeoniflorin by heat treatment during extraction and processing of an active ingredient of peony. However, since it has a problem of aggregation or precipitation due to the passage of time, temperature changes and light irradiation after extraction, it had a problem in stability when applied to products such as cosmetics, food, etc.

Microcapsules (emulsion) are in a water-oil phase mixture which is stabilized by a surfactant lowering the energy of the interface (phase) between the double layer having hydrophilic and hydrophobic properties. Microcapsules are usually spherical in both oil/water phases, and if there is no external energy supply, they are stable for several hours to several days. Microcapsules are generally used to acquire a high level of solubility of a material that is differentially solubilized in an oil or water phase.

To this end, conventionally, in almost all cases, polyols have been used as a surfactant, and the polyols include glycerol, propylene glycol, 1,3-butyrene glycol, and polyethylene glycol. However, these are simple surfactants, and are difficult to be used for high solubility of a material.

A glyceryl acrylate/acrylic acid copolymer has extremely high hydrophilicity, a molecular weight of more than 1.67E-18 g (1 million daltons), and generally includes a polyacrylic acid skeleton partially esterified with glycerin (typically approximately 50% esterified). The glyceryl acrylate/acrylic acid copolymer forms a clathrate that traps water, and is considered to impart lubricating and moisturizing properties to the skin upon release.

SUMMARY OF THE INVENTION

The present invention is directed to providing a cosmetic composition which includes microcapsule particles (1 to 1,000 μm) stabilized by encapsulating a peony extract as an active ingredient, which is useful for skin, with a biocopolymer, and a fibrous protein surrounding the particles in a matrix form, a method of preparing the cosmetic composition, and the use of the cosmetic composition for improving a skin condition.

To solve the above-described problem, the present invention provides a cosmetic composition for improving a skin condition, which includes microcapsules consisting of a biocopolymer encapsulating an active ingredient, a basic amino acid and a polyglycerly ester, and a fibrous protein stabilizing the microcapsules.

In addition, the microcapsule has a size of 2 μm or less.

In addition, the biocopolymer is one or more selected from the group consisting of an acrylate/acrylic acid copolymer; an acrylate/dimethicone copolymer; an acrylate/stearate-20 methacrylate copolymer; an acrylate/octylacrylamide copolymer; an acrylate/palmeth-25 acrylate copolymer; an acrylate copolymer; an acrylic acid/acrylonitrogens copolymer; an acrylamide/sodium acrylate copolymer; and an acrylamide/sodium acryloyldimethyltaurate copolymer.

In addition, the basic amino acid is one or more selected from the group consisting of lysine; arginine; and histidine.

In addition, the active ingredient includes paeoniflorin or a cosmetologically acceptable salt thereof.

In addition, the polyglyceryl ester is one or more selected from the group consisting of polyglyceryl stearate; polyglyceryl myristate; polyglyceryl laurate; polyglyceryl oleate; polyglyceryl isostearate; polyglyceryl distearate; and polyglyceryl tristearate.

In addition, the fibrous protein is one or more selected from the group consisting of lecithin and gelatin.

In addition, the present invention provides a method of preparing a cosmetic composition for improving a skin condition, which includes: preparing a homogeneous mixture by heating and dissolving a biocopolymer, a basic amino acid and an active ingredient; preparing microcapsules by adding a polyglyceryl ester to the previous step and cooling and stirring the resulting mixture at high-speed; and stabilizing the microcapsules by adding the fibrous protein to the previous step.

In addition, the weight ratio of the biocopolymer and the basic amino acid may be 1:1.

In addition, the weight ratio of the biocopolymer and the polyglyceryl ester may be 1:5.

In addition, the weight ratio of the biocopolymer and the fibrous protein may be 1:1.

In addition, the improvement of a skin condition may refer to improvement in skin wrinkles, skin renewal, improvement in skin elasticity, inhibition of skin aging, skin wound regeneration, acne improvement or skin whitening.

The present invention relates to a cosmetic composition which includes microcapsule particles (1 to 1,000 μm) stabilized by encapsulating a peony extract as an active ingredient, which is useful for skin, with a biocopolymer, and a fibrous protein surrounding the particles in a matrix form, a method of preparing the cosmetic composition, and the use of the cosmetic composition for improving a skin condition. Hereinafter, the present invention will be described in further detail.

The present invention relates to a cosmetic composition, which includes microcapsule particles in which a peony extract as an active ingredient is encapsulated with a biocopolymer, and a fibrous protein which surrounds the microcapsules in a matrix form so as to prevent aggregation thereof to stably maintain them in the cosmetic composition for a long time.

In one embodiment of the present invention, the present invention relates to a cosmetic composition for improving a skin state, which contains a peony extract as an active ingredient.

In the present invention, microcapsules may be formed of a biocopolymer, a polyglyceryl ester, and a basic amino acid.

In the present invention, the biocopolymer may be one or more selected from the group consisting of an acrylate/acrylic acid copolymer, an acrylate/dimethicone copolymer, an acrylate/stearate-20 methacrylate copolymer, an acrylate/octyl acrylamide copolymer, an acrylate/palmeth-25 acrylate copolymer, an acrylate copolymer, an acrylic acid/acrylonitrogens copolymer, an acrylamide/sodium acrylate copolymer, an acrylamide/sodium acryloyldimethyl taurate copolymer, crosspolymer-2, and polyvinyl alcohol, but the present invention is not limited thereto.

In the present invention, the basic amino acid may be one or more selected from lysine, arginine and histidine, but the present invention is not limited thereto.

In the present invention, the polyglyceryl ester may be one or more selected from the group consisting of polyglyceryl stearate; polyglyceryl myristate; polyglyceryl laurate; polyglyceryl oleate; polyglyceryl isostearate; polyglyceryl distearate; and polyglyceryl tristearate, but the present invention is not limited thereto.

In the present invention, the fibrous protein may be one or more selected from the group consisting of collagen, gelatin and lecithin, but the present invention is not limited thereto.

In the present invention, the cosmetic composition may have a structure in which microcapsule particles, which are formed by preparing a mixture by mixing a mixture of a biocopolymer and a basic amino acid with an active ingredient and adding a polyglyceryl ester as a template, are surrounded by a fibrous protein in a matrix form that is sequentially added for particle stabilization.

In the present invention, the template refers to a spherical surfactant used to induce spontaneous or heat-triggered polymerization, and is a form that can induce polymerization occurring in a spherical shape along the surface of the surfactant.

In the present invention, the microcapsule has a spherical shape observed under a microscope, and has a diameter of 1 to 1,000 μm.

In the present invention, the content of the biocopolymer component may be 0.001 to 5.0 wt %, 0.001 to 4.0 wt %, 0.001 to 3.0 wt %, 0.001 to 2.0 wt %, 0.001 to 1.0 wt %, or 0.001 to 0.1 wt %, and preferably 0.08 wt %, with respect to the total weight of the composition.

In the present invention, the content of the basic amino acid component may be 0.001 to 5.0 wt %, 0.001 to 4.0 wt %, 0.001 to 3.0 wt %, 0.001 to 2.0 wt %, 0.001 to 1.0 wt %, or 0.001 to 0.1 wt %, and preferably 0.08 wt %, with respect to the total weight of the composition.

In the present invention, the content of the polyglyceryl ester may be 0.001 to 5.0 wt %, 0.001 to 4.0 wt %, 0.001 to 3.0 wt %, 0.001 to 2.0 wt %, or 0.001 to 1.0 wt %, and preferably 0.4 wt %, with respect to the total weight of the cosmetic composition.

In the present invention, the mixing ratio of the basic amino acid to the biocopolymer may be 0.01 to 5.0:1, 0.01 to 4.0:1, 0.01 to 3.0:1, 0.01 to 2.0:1, 0.01 to 1.0:1, or 0.01 to 0.1:1, and preferably 1.0:1 by weight.

In the present invention, the mixing ratio of the polyglyceryl ester to the biocopolymer may be 1 to 10:1, 1 to 7:1, 1 to 5:1, or 1 to 2:1, and preferably 5:1 by weight.

The term "extract" used herein refers to a solvent crude extract, a specific solvent soluble extract (solvent fraction), and a solvent fraction of the solvent crude extract, and the peony extract may be in the form of a solution, concentrate or powder.

In the present invention, the peony may be one or more selected from the group consisting of its roots, stems, leaves and flowers, and preferably, the flowers of the peony.

In the present invention, the peony extract may be a crude extract obtained by extraction with one or more solvents selected from the group consisting of water and linear or branched C1-C4 alcohols.

In the present invention, when a mixture of water and an alcohol is used as a solvent for preparing the peony crude extract, the aqueous solution may contain the linear or branched C1-C4 alcohol at 10% or more and less than 100% (v/v), 20% or more and less than 100% (v/v), 30% or more and less than 100% (v/v), 40% or more and less than 100% (v/v), 50% or more and less than 100% (v/v), 60% or more and less than 100% (v/v), or 70% or more and less than 100% (v/v).

In the present invention, the aqueous alcohol solution may be one or more selected from the group consisting of an aqueous methanol solution, an aqueous ethanol solution, an aqueous propanol solution, and an aqueous butanol solution.

In the present invention, the peony extract may be a solvent fraction prepared by fractionating the solvent crude extract with an additional solvent, which may be, for example, one or more solvents selected from the group consisting of ethyl ether, ethyl acetate and butanol.

In one embodiment of the present invention, the peony extract may be a solvent fraction prepared by fractionating the solvent crude extract which is prepared by extracting peony with one or more solvents selected from the group consisting of water and linear or branched C1-C4 alcohols with one or more solvents selected from the group consisting of ethyl ether, ethyl acetate and butanol.

A process of preparing the peony extract according to the present invention will be described in further detail below:

Peony is cut into pieces, washed with water to remove foreign matter, and then dried, followed by reflux extraction with an approximate 5 to 20-fold volume, and preferably a 7 to 15-fold volume, of an extraction solvent with respect to the weight of the peony. After extraction, the resulting extract is filtered, thereby collecting a filtrate. An extraction temperature may be 40 to 110° C., and preferably, 55 to 90° C., but the present invention is not limited thereto.

An extraction process may be performed once or repeated several times, and according to one exemplary embodiment of the present invention, after first extraction, reextraction may be selected, and this is to prevent a decrease in extraction efficiency with only the first extraction due to loss in the case of a herbal medicine extract being produced in large quantities because of a high moisture content of a herbal medicine although effectively filtered. In addition, as a result of verifying the extraction efficiency for each step, it was revealed that approximately 80 to 90% of the total extraction amount was obtained through second extraction.

In one embodiment of the present invention, when the extraction process is repeated twice, the obtained residue is subjected to reflux extraction again with an approximate 5 to 15-fold volume, and preferably, an 8 to 12-fold volume, of an extraction solvent. After extraction, the resulting product is filtered, combined with the previously-obtained filtrate and concentrated under reduced pressure, thereby preparing a peony extract. As such, extraction efficiency may increase through two-step extraction and by mixing the filtrates obtained by respective extractions, but the extract of the present invention is not limited by the number of extractions.

In the present invention, when the amount of the solvent used in the preparation of the peony extract is too small, stirring is difficult, and extraction efficiency decreases due to low solubility of the extract. When the amount of the solvent used in the preparation of the peony extract is too large, as the amount of a solvent used in a subsequent purification step becomes larger, the solvent is not economical and may have a handling problem. Therefore, the amount of a solvent used herein is in the above-described range.

In order to adjust the content of a remaining lower alcohol to be suitable for being used as a pharmaceutical raw material, the filtered extract obtained as described above may be azeotropically concentrated 1 to 5 times, and preferably 2 to 3 times with approximately 10 to 30-fold, preferably, 15 to 25-fold, and more preferably approximately 20-fold more water than the total content of the concentrate, homogenously suspended with the same amount of water and then freeze-dried, resulting in the preparation of a powder-type peony extract.

The extraction method used herein may be any method that is conventionally used, which may be, for example, cold sedimentation, hot water extraction, ultrasonic extraction or reflux cooling extraction, but the present invention is not limited thereto.

In the present invention, the peony extract may include 90% or more of paeoniflorin or a cosmetologically acceptable salt thereof.

In the present invention, the paeoniflorin ($C_{23}H_{28}O_{11}$) is a material having a molecular weight of 480, and represented by Formula 1 below.

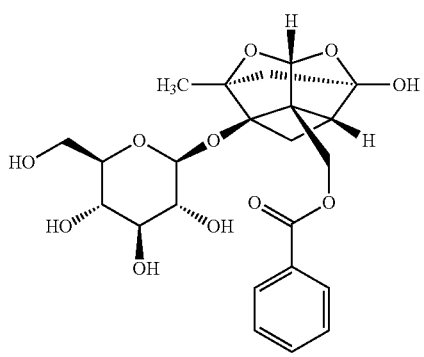

[Formula 1]

In the present invention, the paeoniflorin may be present in a form of a cosmetologically acceptable salt.

In the present invention, the salt may be any cosmetologically acceptable salt without particular limitation, and may be, for example, hydrochloric acid, sulfuric acid, nitric acid, phosphoric acid, hydrofluoric acid, hydrobromic acid, formic acid, acetic acid, tartaric acid, lactic acid, citric acid, fumaric acid, maleic acid, succinic acid, methanesulfonic acid, benzenesulfonic acid, toluenesulfonic acid or naphthalenesulfonic acid, but the present invention is not limited thereto.

In the present invention, the mixing ratio of paeoniflorin to the biocopolymer may be 0.01 to 5.0:1, 0.01 to 4.0:1, 0.01 to 3.0:1, 0.01 to 2.0:1, 0.01 to 1.0:1, 0.01 to 0.1:1, and preferably, 1.0:1 by weight.

In the present invention, the cosmetic composition may further include a thickener.

In the present invention, the thickener may be one or more selected from the group consisting of glycerin, butylene glycol, and a carbomer, but the present invention is not limited thereto.

In the present invention, the cosmetic composition may further include a preservative.

In the present invention, the preservative may be one or more selected from the group consisting of 1,2-hexanediol and hydroxyacetophenone, but the present invention is not limited thereto.

The term "improvement of a skin condition" used herein may refer to improvement in skin wrinkles, skin renewal, improvement in skin elasticity, inhibition of skin aging, skin wound regeneration, acne improvement or skin whitening, but the present invention is not limited thereto.

The term "cosmetologically effective amount" used herein refers to an amount that is sufficient to achieve skin improvement efficacy of the above-described composition of the present invention.

The cosmetic composition of the present invention may be prepared in any formulation which is conventionally prepared in the art, and may be formulated in various forms, for example, a solution, a suspension, an emulsion, a paste, a gel, a cream, a lotion, a powder, a soap, a surfactant-containing cleanser, an oil, a powder-type foundation, an emulsion-type foundation, a wax-type foundation and a spray, but the present invention is not limited thereto. More specifically, the cosmetic composition of the present invention may be formulated in the form of a softening toner, a nourishing toner, a nourishing cream, a massage cream, an essence, an eye cream, a cleansing cream, a cleansing foam, a cleansing water, a pack, a spray or a powder.

When the cosmetic composition of the present invention is prepared in the form of a paste, cream or gel, an animal oil, a vegetable oil, wax, paraffin, starch, tragacanth, a cellulose derivative, polyethylene glycol, silicone, bentonite, silica, talc or zinc oxide may be used as a carrier component.

When the cosmetic composition of the present invention is prepared in the form of a powder or spray, lactose, talc, silica, aluminum hydroxide, calcium silicate or polyamide powder may be used as a carrier component, and particularly, when prepared in the form of a spray, a propellant such as chlorofluorohydrocarbon, propane/butane or dimethyl ether may be further added.

When the cosmetic composition of the present invention is prepared in the form of a solution or emulsion, a solvent, a solubilizer or an emulsifier, for example, water, ethanol, isopropanol, ethyl carbonate, ethyl acetate, benzyl alcohol, benzyl benzoate, propylene glycol, 1,3-butylglycol oil, glycerol aliphatic ester, polyethylene glycol or an aliphatic ester of sorbitan, is used as a carrier component.

When the cosmetic composition of the present invention is prepared in the form of an emulsion, a liquid diluent such as water, ethanol or propylene glycol, a suspending agent such as ethoxylated isostearyl alcohol, polyoxyethylene sorbitol ester and polyoxyethylene sorbitan ester, microcrystalline cellulose, aluminum methhydroxide, bentonite, agar or tragacanth may be used as a carrier component.

When the cosmetic composition of the present invention is prepared in the form of a surfactant-containing cleanser, an aliphatic alcohol sulfate, an aliphatic alcohol ether sulfate, sulfosuccinic acid monoester, isethionate, an imidazolium derivate, methyl taurate, sarcosinate, an aliphatic amide ether sulfate, an alkyl amidobetaine, an aliphatic alcohol, an aliphatic glyceride, an aliphatic diethanolamide, a vegetable oil, a lanolin derivative or ethoxylated glycerol fatty acid ester may be used as a carrier component.

In addition to the active ingredient, the cosmetic composition of the present invention may also include conventionally used components, for example, conventional additives such as an antioxidant, a stabilizer, a solubilizer, a vitamin, a pigment and a fragrance.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which:

FIG. 1 is a schematic diagram showing the flow chart and structure of a cosmetic composition according to one embodiment of the present invention;

FIG. 2 is a set of microscopic images of cosmetic compositions having microcapsules and a matrix according to one example and comparative examples of the present invention;

FIG. 3 is a graph showing the result of measuring expression levels of HSP-related signaling genes according to one embodiment of the present invention;

FIG. 4 shows the result of measuring expression levels of HSPs according to a content according to one embodiment of the present invention;

FIG. 5 shows the result of measuring expression levels of HSPs over time according to one embodiment of the present invention;

FIG. 6 shows the result of an experiment of confirming the resistance of cells to oxidative stress due to HSP induction according to one embodiment of the present invention;

FIG. 7 shows the result of an experiment of confirming the resistance of cells to oxidative stress due to HSP induction according to one embodiment of the present invention; and FIG. 8 is a schematic diagram showing the skin protective effect of the cosmetic composition prepared according to one embodiment of the present invention.

DETAILED DESCRIPTION OF EXEMPLARY EMBODIMENTS

Hereinafter, the present invention will be described in further detail with reference to the following examples. However, these examples are merely provided to exemplify the present invention, and the scope of the present invention is not limited by the following examples.

Preparation Example 1. Preparation of Peony Extract and Detection of Paeoniflorin 100 g of dried peony petals were cut into small pieces, added to and mixed with a 10-fold volume of water solvent (1 L), followed by soaking for 1 hour. While heating to 100° C., the mixture was extracted by being refluxed in a reflux condenser for 2 hours, and then subjected to second extraction for 1 hour. The extracted liquid was filtered with a gauze filter to remove a solid. After extraction, the resulting product was vacuum-dried. The final extracted solid was detected to be 0.02 g/L. The final extracted solid was dissolved at 1 mg/ml, and then analyzed by high performance liquid chromatography (HPLC), confirming that the concentration of the paeoniflorin contained in the solid was 0.93 mg/ml.

Preparation Example 2. Preparation of Microcapsule-Matrix Composition

The schematic diagram of the prepared cosmetic composition is shown in FIG. 1. Specifically, 0.08 wt % each of an acrylate/acrylic acid copolymer and arginine were uniformly dispersed in distilled water and dissolved at 50° C. for 30 minutes. 0.08 wt % of the peony extract was added to the resulting solution, and then stirred at room temperature for 30 minutes. Afterward, 0.4 wt % of polyglyceryl oleate was added to the resulting product, and then stirred using a homogenizer at 2,000 to 8,000 RPM while cooling to 4° C., thereby forming microcapsules. For long-term stabilization and long-term prevention of aggregation, 0.09 wt % of hyaluronate was added to the formed microcapsules and slowly stirred at room temperature and a speed of 1,000 RPM or less, thereby forming a matrix. After the prepared cosmetic composition was observed using a microscope and compared with cosmetic composition of an example, the result is shown in FIG. 2. Comparative Examples 1 and 2 were prepared in the same manner as used in the example, except that components listed in Table 1 were used.

As confirmed in FIGS. 1 and 2, it was seen that the cosmetic composition is a formulation containing microcapsules protecting the active ingredient and a matrix stabilizing the microcapsules.

TABLE 1

| Component | Use | Example 1 | Comparative Example 1 | Comparative Example 2 | Comparative Example 3 |
|---|---|---|---|---|---|
| | | (wt %) | | | |
| Distilled water | Solvent | 69.091 | 69.171 | 69.171 | 69.491 |
| Paeoniflorin | Active ingredient | 0.0800 | 0.0800 | 0.0800 | 0.0800 |
| Glycerin | Thickener | 14.714 | 14.714 | 14.714 | 14.714 |
| Methyl propanediol | Excipient | 7.510 | 7.510 | 7.510 | 7.510 |
| Butyl glycol | Thickener | 5.644 | 5.644 | 5.644 | 5.644 |
| 1,2-hexanediol | Preservative | 1.530 | 1.530 | 1.530 | 1.530 |
| Allantoin | Skin conditioner | 0.100 | 0.100 | 0.100 | 0.100 |
| Trehalose | Skin conditioner | 0.500 | 0.500 | 0.500 | 0.500 |
| Glyceryl acrylate/acrylic acid copolymer | Biocopolymer | 0.080 | — | 0.080 | 0.080 |
| Polyglycelyl-oleate | Polyglyceryl ester | 0.400 | 0.400 | 0.400 | — |
| Arginine | Basic amino acid | 0.080 | 0.080 | — | 0.080 |
| Carbomer | Thickener | 0.181 | 0.181 | 0.181 | 0.181 |
| Hyaluronate | Fibrous protein | 0.090 | 0.090 | 0.090 | 0.090 |
| Total | — | 100 | 100 | 100 | 100 |

Comparing Example 1, and Comparative Examples 1 and 2, in the formulation of Example 1, a clear microcapsule containing the active ingredient is shown under a microscope. However, in Comparative Examples 1 and 2, it was confirmed that the active ingredient is agglomerated with other components and then dispersed, without formation of microcapsules.

Experimental Example 1. Measurement of Stability of Formed Microcapsule-Matrix

To measure the stability of the microcapsules, a composition was prepared in the same manner as in the examples, except that the hyaluronate of the hyaluronate-added composition (Example 1) was substituted with each of the same amounts of lecithin and gelatin, which are similar thickeners, and then the change in size of microcapsule particles was measured using a dynamic light scattering (DLS) device for 8 weeks. The result is shown in Table 2.

TABLE 2

| Experimental | Change in particle size (average, μm) | | | | Change rate |
|---|---|---|---|---|---|
| group | 1 week | 3 weeks | 6 weeks | 8 weeks | (%) |
| Control | 1.38 | Not measurable | Not measurable | Not measurable | Not formed |
| Hyaluronate | 1.1 | 1.12 | 1.08 | 1.14 | 100.9 |
| Lecithin | 1.25 | 2.94 | 8.35 | 13.92 | 529.2 |
| Gelatin | 1.34 | 1.85 | 3.43 | 3.86 | 195.5 |

As a control, Comparative Example 3 was used, and a composition of Comparative Example 3 was prepared in the same manner as in the examples, except that the components listed in Table 1 are used.

One week after preparation, the size of the particles in Example 1 was 1.21 μm on average, and an error range was 0.34 μm.

At one, three, six and eight weeks after formulation, the particle size was measured. When the measured particle is spherical, the size may be measured by calculating a flow rate (k) due to an electromagnetic field, but in the case of amorphous agglomeration, it was detected as unmeasurable because a measured value was not displayed. The rate of change is the change in expressed as a change rate of an average of values measured for 8 weeks with respect to the initial value in percentage (%).

A control showed a completely unstable pattern since the spherical shape of a microcapsule was not observed after one week.

When the microcapsules were stabilized with a hyaluronate, there was almost no change in size for 8 weeks, whereas when the microcapsules were stabilized with lecithin or gelatin, microcapsules were formed but considerably increased in size for 8 weeks so that they agglomerated, indicating instability.

Experimental Example 2. Expression Levels of HSP-Related Signaling Genes (Real-Time q-PCR)

Human skin keratinocytes (BS cells) were obtained from the Korean Cell Line Bank (KCLB). For cell culture, cells were seeded at 10,000 cells/well in a 24-well plate as a cell culture dish containing a RPMI cell culture medium supplemented with 10% fetal bovine serum (FBS) and a 1% antibiotic, and then stabilized in an incubator for 24 hours at 37° C.

The composition of Example 1 was inoculated in units of 100 μL on day 2, and after inoculation, the morphology of cells and related gene expression were examined. Specifically, the experiment was performed for controls (Comparative Examples 1 and 2) and the treatment group (Example). 100 μL of a sample per mL of the medium was treated for each group, and cultured for 24 hours at 37° C. and 5% $CO_2$, followed by confirmation of whether a human HSP was expressed.

As a stress condition, 100 μM $H_2O_2$ was additionally added to each 100 μL per mL of the medium, and then incubated for 24 hours.

To check whether a human HSP was expressed or not, real-time gene amplification expression tests were conducted for HSP40, HSP90, HSP70 and HSP27 genes. Specifically, primers for each gene were constructed, the genes were amplified up to 49 cycles based on the primers using Taq polymerase activity, and the gene expression rates were detected in real time. The result is shown in FIG. 3.

TABLE 3

| SEQ ID NO: | Name | Sequence list | Remark |
|---|---|---|---|
| 1 | HSP40 | ggaggagctgttccatg | |
| 2 | HSP90 | ggagacctcgctat | |
| 3 | HSP70 | caccaagaagatgaaaatc | |
| 4 | HSP27 | acaagctctgcttatc | |

TABLE 4

| Control | | Treatment group | | | | | | | |
|---|---|---|---|---|---|---|---|---|---|
| Control | | Stress− | | | | Stress+ | | | |
| (Stress−) | Stress+ | Hsp40 | Hsp90 | Hsp70 | Hsp27 | Hsp40 | Hsp90 | Hsp70 | Hsp27 |
| 100 | 283.45 | 174.35 | 212.4 | 244.75 | 174.56 | 256.87 | 331.46 | 441.54 | 384.54 |

It was confirmed that each gene was expressed in the experimental environment without a problem, and first confirmed that there was no problem in terms of amplification efficiency over time. In addition, as confirmed in FIG. 3 and Table 4, it was seen that, under a stress condition (Oxidative stress: 100 μM $H_2O_2$-treated group), the total HSP expression increased approximately 2.8-fold, and according to the treatment with the example, a 1.5 to 2.4-fold higher gene expression rate than that under a stress condition, which is a stable expression rate, was shown. Such a gene expression rate was further amplified when stress was applied and the example was treated. The overall gene expression rate was amplified by 2.9 to 4.4-fold, confirming that the responsiveness to oxidative stress was increased approximately 2-fold, and particularly, it was confirmed that the expression rates of HSP70 and HSP27 genes, which are known to be important for the defense mechanism against oxidative stress, are greatly increased.

Experimental Example 3. HSP Expression Level (Western Blotting)

3-1. Expression Level According to Content

Human skin keratinocytes (BS cells) were obtained from the Korean Cell Line Bank (KCLB). For cell culture, cells were seeded at 40,000 cells/well in a 6-well plate as a cell culture dish containing a RPMI cell culture medium supplemented with 10% fetal bovine serum (FBS) and a 1% antibiotic, and then stabilized in an incubator for 24 hours at 37° C. A sample was inoculated in units of 200 μl on day 2, and after inoculation, cell morphology and related gene expression were examined.

An experiment was performed on controls (Comparative Examples 1 and 2) and the treatment group (Example 1). For each group, addition of 100 μL of a sample per mL of the medium was set as 10 wt %, and 10 to 50 wt % of the sample was added to the cells, and incubated for 24 hours at 37° C. in a 5% $CO_2$ condition. One hour after incubation, the expression of a human HSP was detected. In this experiment, stress was not applied to the cells.

Whether a change associated with human HSP expression affects a change in intracellular protein level was examined. Specifically, one hour after treatment of different contents (10 wt %, 20 wt %, 30 wt %, 40 wt % and 50 wt %) of a treated sample affecting HSP expression of the cosmetic composition of Example 1, 200 μL of cell lysis buffer was added to obtain cells, and then proteins were isolated at 100° C. for 10 minutes by adding 500 μL of mercaptoethanol. Proteins were separated according to a molecular weight by applying a charge to an SDS-PAGE environment for 3 hours, and detection was performed by observing the presence or absence of the protein by treating an HRP-tagged antibody. The result is shown in FIG. 4.

As shown in FIG. 4, the change in extract content showed a slight increase in HSP27, but other HSPs did not show significant increases in expression level. These results confirm that the addition of DRBASE in a stress-free environment does not significantly affect cells.

3-2. Measurement of Change in Expression Level Over Time Depending on the Presence or Absence of Stress Human skin keratinocytes (BS cells) were obtained from the Korean Cell Line Bank (KCLB). For cell culture, cells were seeded at 40,000 cells/well in a 6-well plate as a cell culture dish containing a RPMI cell culture medium supplemented with 10% fetal bovine serum (FBS) and a 1% antibiotic, and then stabilized in an incubator for 24 hours at 37° C.

A sample was inoculated in units of 200 μl on day 2, and after inoculation, cell morphology and related gene expression were examined. An experiment was performed on controls (Comparative Examples 1 and 2) and the treatment group (Example 1). For each experimental group, addition of 100 μL of a sample per mL of the medium was set as 10 wt %, and 10 to 50 wt % of the sample was added to the cells, and incubated for 24 hours at 37° C. in a 5% $CO_2$ condition. One hour after incubation, the expression of human HSPs was detected. As a stress condition, 100 μM $H_2O_2$ was added to each 100 μL per mL of the medium and cultured for the same time. The protein change after treatment was detected in the same manner as the western blotting.

To confirm whether there is a change in stability of a protein over the actual treatment time depending on the presence or absence of stress applied to cells, after oxidative stress (100 μM $H_2O_2$ treatment) was applied to cells under the same conditions, the intracellular concentration of HSPs was measured. The result is shown in FIG. 5.

As seen in FIG. 5, HSPs drastically increasing after the application of oxidative stress showed a drastic decrease in the initial concentration after one and a half hours. The drastic decrease in HSPs was greatly increased when the cosmetic composition of an example was treated, and particularly, a significant effect of continuously maintaining a high HSP concentration at 30 minutes, which is the early state of the treatment, until about 3 hours was shown. As a result, in the case in which the cosmetic composition of the example was treated, but oxidative stress was not applied to cells, it was confirmed that it does not particularly affect HSP expression, whereas the treatment of the cosmetic composition of the example significantly maintains HSPs under an oxidative stress condition in which the HSP expression is rapidly reduced.

Accordingly, it is considered that the example shows an insignificant expression-inducing effect on HSP under a stress-free condition, but shows a very potent HSP expression-inducing effect under an oxidative stress condition such as $H_2O_2$ treatment.

Experimental Example 4. Oxidative Stress-Induced Cell Aging

It was confirmed whether the HSP induction increases resistance of cells against a high concentration of oxidative stress. Specifically, while increasing the concentration of oxidative stress, cells were cultured for 1 hour at 37° C. in 5% $CO_2$ condition, and then cell viability was assessed by MTT assay. The result is shown in FIG. 6.

As seen in FIG. 6, the cell viability that had no change at a low concentration of 50 μM showed significant toxicity from 200 mM, whereas in the group treated with the cosmetic composition of the example, it was confirmed that cells endured a high oxidative stress of 200 μM. It was confirmed that the treatment of the cosmetic composition of the example inhibits cell aging even when a low concentration of oxidative stress (100 mM) was treated for a long period of time.

In addition, as confirmed in FIG. 7, after the application of oxidative stress, for 14 days, it was confirmed that the morphology of cells showing cell growth and senescence traits (white arrows) is significantly reduced in the group treated with the cosmetic composition of the example.

The present invention relates to a cosmetic composition which includes microcapsule particles (1 to 1000 μm) which are stabilized by encapsulating a peony extract as an active ingredient, which is useful for skin, with a biocopolymer, and a fibrous protein surrounding the particles in a matrix form, a method of preparing the cosmetic composition and the use of the cosmetic composition for improving a skin condition.

It will be apparent to those skilled in the art that various modifications can be made to the above-described exemplary embodiments of the present invention without departing from the spirit or scope of the invention. Thus, it is intended that the present invention covers all such modifications provided they come within the scope of the appended claims and their equivalents

What is claimed is:

1. A cosmetic composition comprising microcapsules consisting of a biocopolymer encapsulating an active ingredient, a basic amino acid and a polyglycerly ester, and a fibrous protein surrounding each microcapsule in a matrix form to stablize the microcapsules, wherein the biocopolvmer and the basic amino acid are in a 1:1 weight ratio, and the biocopolymer and the fibrous protein are in a 1:1 weight ratio.

2. The cosmetic composition of claim 1, wherein the microcapsule has a size of 2 μm or less.

3. The cosmetic composition of claim 1. wherein the biocopolymer is one or more selected from the group consisting of an acrylate/acrylic acid copolymer; an acrylate/dimethicone copolymer; an acrylate/stearate-20 methacrylate copolymer; an aciylate/octylaciylamide copolymer; an acrylate/palmeth-25 acrylate copolymer; an acrylate copolymer; an acrylic acid/acrylonitrogens copolymer; an acrylamide/sodium acrylate copolymer; and an acrylamide/sodium acryloyldimethyltaurate copolymer.

4. The cosmetic composition of claim 1; wherein the basic amino acid is one or more selected from the group consisting of lysine; arginine; and histidine.

5. The cosmetic composition of claim 1, wherein the active ingredient comprises paeoniflorin or a cosmetologically acceptable salt thereof.

6. The cosmetic composition of claim 1; wherein the polyglyceryl ester is one or more selected from the group consisting of polyglyceryl stearate; polyglyceryl myristate; polyglyceryl laurate; polyglyceryl oleate; polyglyceryl isostearate; polyglyceryl distearate; and polyglyceryl tristearate.

7. The cosmetic composition of claim 1; wherein the fibrous protein is one or more selected from the group consisting of lecithin and gelatin.

8. The cosmetic composition of claim 1. wherein the composition comprises the biocopolymer and the polyglyceryl ester in a 1:5 weight ratio with respect to the total weight of the composition.

* * * * *